(12) United States Patent
Kishiro et al.

(10) Patent No.: US 10,261,051 B2
(45) Date of Patent: Apr. 16, 2019

(54) FLUID MEASURING DEVICE INCLUDING AN ULTRASONIC PROBE HAVING A WEDGE WITH AN ULTRASONIC VIBRATOR

(71) Applicant: FUJI ELECTRIC CO., LTD., Kawasaki-shi (JP)

(72) Inventors: Masami Kishiro, Hino (JP); Noritomo Hirayama, Hino (JP)

(73) Assignee: FUJI ELECTRIC CO., LTD., Kawasaki-shi (JP)

( * ) Notice: Subject to any disclaimer, the term of this patent is extended or adjusted under 35 U.S.C. 154(b) by 406 days.

(21) Appl. No.: 14/938,817

(22) Filed: Nov. 11, 2015

(65) Prior Publication Data

US 2016/0061778 A1 Mar. 3, 2016

Related U.S. Application Data

(63) Continuation of application No. PCT/JP2014/071592, filed on Aug. 18, 2014.

(30) Foreign Application Priority Data

Oct. 23, 2013 (JP) .................................. 2013-220613

(51) Int. Cl.
*G01N 29/024* (2006.01)
*G01F 1/66* (2006.01)
*G01N 29/24* (2006.01)

(52) U.S. Cl.
CPC ............. *G01N 29/024* (2013.01); *G01F 1/66* (2013.01); *G01F 1/662* (2013.01); *G01F 1/667* (2013.01);

(Continued)

(58) Field of Classification Search
CPC .. G01N 29/07; G01N 29/024; G01N 29/2487; G01N 2291/011;

(Continued)

(56) References Cited

U.S. PATENT DOCUMENTS 1,285,715 A * 11/1918 Lack ...................... B61D 41/00
  40/368
4,930,358 A * 6/1990 Motegi ................... G01F 1/662
  73/861.28

(Continued)

FOREIGN PATENT DOCUMENTS

JP S60-61622 U 4/1985
JP 2683159 B2 11/1997

(Continued)

*Primary Examiner* — Jonathan M Dunlap
*Assistant Examiner* — Octavia Hollington
(74) *Attorney, Agent, or Firm* — Rabin & Berdo, P.C.

(57) ABSTRACT

A fluid measuring device in which an ultrasonic probe provided on an outer pipeline surface transmits and receives ultrasonic waves to and from fluid in a pipeline to measure characteristics of the fluid on the basis of propagation time of the ultrasonic waves, features a wedge included in the ultrasonic probe and having an ultrasonic vibrator provided on a wedge surface. The ultrasonic vibrator may be horizontal to a surface contacting the pipeline so that ultrasonic waves enter the fluid vertically. The ultrasonic vibrator may be provided on a wedge surface inclined with respect to an axial direction of the pipeline so that ultrasonic waves enter the fluid obliquely. The fluid measuring device embodiments are capable of measuring fluid characteristics, such as the type and velocity of various fluids, easily and accurately even when it is difficult to allow an ultrasonic signal to pass through the fluid in a pipeline.

5 Claims, 24 Drawing Sheets

(52) U.S. Cl.
CPC ... *G01N 29/2487* (2013.01); *G01N 2291/011* (2013.01); *G01N 2291/02836* (2013.01); *G01N 2291/101* (2013.01)

(58) Field of Classification Search
CPC .... G01N 2291/02836; G01N 2291/101; G01F 1/66; G01F 1/662; G01F 1/667
USPC ... 73/597, 602, 622, 861.23–861.31, 27, 28, 73/29, 31, 862.28
See application file for complete search history.

(56) References Cited

U.S. PATENT DOCUMENTS

| | | | | |
|---|---|---|---|---|
| 5,280,728 | A * | 1/1994 | Sato | G01F 1/667 73/861.28 |
| 5,533,408 | A | 7/1996 | Oldenziel et al. | |
| 6,365,873 | B1 * | 4/2002 | Smartt | B23K 31/125 219/130.01 |
| 7,000,485 | B2 * | 2/2006 | Ao | G01F 1/662 73/861.29 |
| 7,077,012 | B2 * | 7/2006 | Hirayama | G01F 1/662 73/861.25 |
| 7,412,902 | B2 * | 8/2008 | Wiest | G01F 1/662 73/861.25 |
| 2005/0154307 | A1 * | 7/2005 | Hirayama | G01F 1/662 600/453 |
| 2007/0151362 | A1 * | 7/2007 | Mori | G01F 1/663 73/861.27 |

FOREIGN PATENT DOCUMENTS

| | | |
|---|---|---|
| JP | H11-94613 A | 4/1999 |
| JP | 4687293 B2 | 5/2011 |

* cited by examiner

FLUID MEASURING DEVICE INCLUDING AN ULTRASONIC PROBE HAVING A WEDGE WITH AN ULTRASONIC VIBRATOR

CROSS-REFERENCE TO RELATED APPLICATION(S)

This non-provisional Application for a U.S. Patent is a Continuation of International Application PCT/JP2014/071592 filed Aug. 18, 2014, which claims priority from JP PA 2013-220613 filed Oct. 23, 2013, the entire contents of both of which are hereby incorporated by reference.

BACKGROUND OF THE INVENTION

1. Field of the Invention

The present invention relates to a fluid measuring device capable of measuring fluid characteristics such as the type and velocity of various fluids easily and accurately even when it is difficult to allow an ultrasonic signal to pass through the fluid in a pipeline.

2. Background of the Related Art

Gas pipeline for supplying town gas and pipelines such as water or sewage pipelines are buried under the ground. When construction works are performed in a place where pipelines are buried, these pipelines may be exposed and it may be difficult to identify the type of the exposed pipeline. In such a case, it is necessary to determine the type of the exposed pipeline by determining the type of fluid flowing through the pipeline (for example, the type of fluid such as town gas, water, or air) and to take measures appropriate for each type of pipeline.

As a conventional method of determining the type of fluid in a pipeline, a method of forming a hole in a pipeline and extracting the fluid through the hole is known. According to another method of determining the type of fluid in a pipeline, a neutron moisture meter is used. This method can determine the fluid type without breaking a pipeline. As still another method of determining the type of fluid in a pipeline, Japanese Patent Application Publication No. H11-94613 (Patent Literature 1) discloses a method of determining the fluid type based on transmission intensity of ultrasonic waves. Moreover, Japanese Patent No. 4687293 (Patent Literature 2) discloses a method of measuring a flow rate distribution of liquid in a pipeline by allowing ultrasonic waves to pass through the pipeline without breaking the pipeline.

However, the method of determining the type of a fluid in a pipeline by extracting internal fluid through a hole requires a pipeline recovery operation of blocking the hole after the type of fluid in the pipeline is determined, which incurs a considerable time and labor.

Moreover, the method of determining the type of fluid in the pipeline using a neutron moisture meter can identify the presence of water only. Thus, the type of fluid that can be identified is limited, and it is difficult to determine a sufficient number of types of fluid.

Further, the method of determining the type of fluid in the pipeline using the transmission intensity of ultrasonic waves, disclosed in Patent Literature 1 requires an ultrasonic probe to be provided in a pipeline, and as a result, a complex piping work is required.

Moreover, when the method disclosed in Patent Literature 2 is applied to gas such as town gas or air, since the transmittance of ultrasonic waves in gas is lower than that in liquid, it is difficult to obtain sufficient measurement accuracy. Further, when a pipeline is old, rusty, or corroded, or has sediments adhering thereto, which makes it difficult for ultrasonic waves to pass through, sufficiently accurate measurement is difficult to implement.

The present invention has been made in view of the above problems, and an object thereof is to provide a fluid measuring device capable of measuring fluid characteristics such as the type and velocity of various fluids easily and accurately even when it is difficult to allow an ultrasonic signal to pass through the fluid in a pipeline.

SUMMARY OF THE INVENTION

In order to solve the problems and attain the object, according to an aspect of the present invention, there is provided a fluid measuring device in which an ultrasonic probe provided on an outer pipeline surface transmits and receives ultrasonic waves to and from fluid in a pipeline to thereby measure characteristics of the fluid on the basis of a propagation time of the ultrasonic waves having propagated through the fluid, wherein the ultrasonic probe has a wedge in which an ultrasonic vibrator is provided on a wedge surface horizontal to a surface contacting the pipeline so that ultrasonic waves enter the fluid vertically, and the wedge has a vibrator surface on which the ultrasonic vibrator is provided and a pipeline contacting surface provided in contact with the outer pipeline surface horizontally to the vibrator surface, in a cross-section vertical to an axial direction of the pipeline, and a length of the pipeline contacting surface in the cross-section vertical to the axial direction is smaller than a length of the vibrator surface in the cross-section vertical to the axial direction.

In the fluid measuring device according to the above aspect of the present invention, the wedge may have a wedge side surface that connects the vibrator surface and the pipeline contacting surface in the cross-section vertical to the axial direction of the pipeline, and the wedge side surface may have an inclined surface portion that is inclined with respect to a line perpendicular to the vibrator surface and the pipeline contacting surface.

In the fluid measuring device according to the above aspect of the present invention, the ultrasonic vibrator may be a pair of ultrasonic vibrators provided on the same wedge to be adjacent in the axial direction of the pipeline.

According to another aspect of the present invention, there is provided a fluid measuring device in which a plurality of ultrasonic probes provided on an outer pipeline surface transmits and receives ultrasonic waves to and from fluid in a pipeline to thereby measure characteristics of the fluid on the basis of a propagation time of the ultrasonic waves having propagated through the fluid, measured by a time measuring unit that measures the time elapsed from transmission to reception of the ultrasonic waves, wherein the ultrasonic probe has a wedge in which an ultrasonic vibrator is provided on a wedge surface inclined with respect to an axial direction of the pipeline so that ultrasonic waves enter the fluid obliquely, and the wedge has a vibrator projection surface on which a vibrator surface having the ultrasonic vibrator provided thereon is projected and a pipeline contacting surface provided in contact with the outer pipeline surface, in a cross-section vertical to the axial direction of the pipeline, and a length of the pipeline contacting surface in the cross-section vertical to the axial direction is smaller than a horizontal length of the vibrator projection surface in the cross-section vertical to the axial direction.

In the fluid measuring device according to the above aspect of the present invention, the wedge may have a wedge side surface that connects the vibrator projection surface and the pipeline contacting surface in the cross-section vertical to the axial direction of the pipeline, and the wedge side surface may have an inclined surface portion that is inclined with respect to a line perpendicular to the pipeline contacting surface.

In the fluid measuring device according to the above aspect of the present invention, the ultrasonic waves generated by the ultrasonic vibrator may be SV-waves with respect to a plane that includes the center of the ultrasonic vibrator and the axis of the pipeline.

In the fluid measuring device according to the above aspect of the present invention, the wedge may have the inclined surface portion and the pipeline contacting surface that are separated in the cross-section vertical to the axial direction.

In the fluid measuring device according to the above aspect of the present invention, the wedge may be formed of a combination of a plurality of materials, and a portion that forms the vibrator surface and a portion that forms the pipeline contacting surface may be formed of different materials.

In the fluid measuring device according to the above aspect of the present invention, the material of the portion that forms the pipeline contacting surface may exhibit higher heat-resistance performance at high or low temperature than the material of the portion that forms the vibrator surface.

In the fluid measuring device according to the above aspect of the present invention, the cross-section of the wedge vertical to the axial direction may have a shape that is bilaterally symmetrical to a central line that passes the axis of the pipeline, and an angle θ of the inclined surface portion to the line perpendicular to the pipeline contacting surface and a value "a" obtained by dividing the length of the pipeline contacting surface in the cross-section vertical to the axial direction by the length of the vibrator surface in the cross-section vertical to the axial direction or the horizontal length of the vibrator projection surface in the cross-section vertical to the axial direction may satisfy a relation of tan 2θ/tan θ<(1+a)/(1−a).

In the fluid measuring device according to the above aspect of the present invention, the value "a" may satisfy a relation of ⅓<a<1.

In the fluid measuring device according to the above aspect of the present invention, the angle θ may satisfy a relation of 0°<θ<45°.

In the fluid measuring device according to the above aspect of the present invention, an ultrasonic absorber may be provided in contact with the outer pipeline surface and around a position in which the wedge makes contact with the outer pipeline surface.

In the fluid measuring device according to the above aspect of the present invention, the ultrasonic absorber may contain tungsten mixed in a base material thereof.

In the fluid measuring device according to the above aspect of the present invention, the ultrasonic absorber may contain magnetic substance mixed in a base material thereof and may be processed in a sheet form.

According to the present invention, one ultrasonic probe provided on the outer pipeline surface transmits and receives ultrasonic waves to and from the fluid in the pipeline. The ultrasonic probe used when measuring the characteristics of the fluid based on the propagation time of the ultrasonic waves having propagated through the fluid has the wedge in which the ultrasonic vibrator is provided on the surface horizontal to the surface contacting the pipeline so that the ultrasonic waves enter the fluid vertically. The wedge has the vibrator surface on which the ultrasonic vibrator is provided and the pipeline contacting surface provided in contact with the outer pipeline surface horizontally to the vibrator surface, in the cross-section vertical to the axial direction of the pipeline. The length of the pipeline contacting surface in the cross-section vertical to the axial direction is smaller than the length of the vibrator surface in the cross-section vertical to the axial direction. Due to such a configuration, the ultrasonic waves emitted from the ultrasonic vibrator concentrate vertically to the pipeline contacting surface and highly dense ultrasonic waves can enter the pipeline. As a result, it is possible to measure fluid characteristics such as the type and velocity of various fluids easily and accurately even when it is difficult to allow an ultrasonic signal to pass through the fluid in a pipeline.

DETAILED DESCRIPTION OF THE INVENTION

Hereinafter, embodiments of the present invention will be described with reference to the accompanying drawings.

First Embodiment—Entire Configuration

Figure 1:
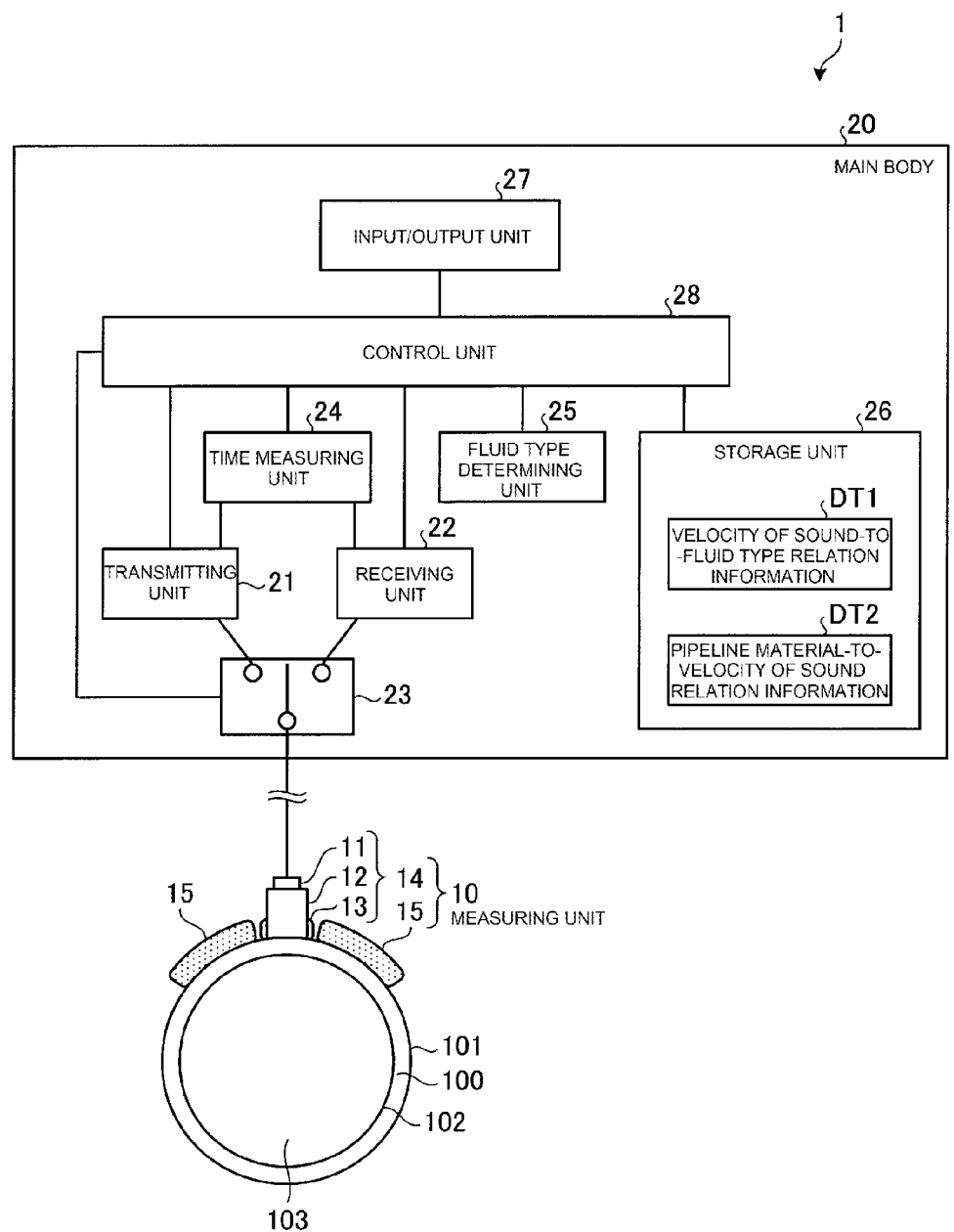
FIG. 1 is a schematic diagram illustrating an entire configuration of a fluid measuring device according to a first embodiment of the present invention.

FIG. 1 is a schematic diagram illustrating an entire configuration of a fluid measuring device according to a first embodiment of the present invention. In FIG. 1, a fluid measuring device 1 determines the type of a fluid 103 flowing through a pipeline 100, which is one of the characteristics of the fluid 103.

As illustrated in FIG. 1, the fluid measuring device 1 includes a measuring unit 10 and a main body 20. The measuring unit 10 includes an ultrasonic vibrator 11 and a wedge 12. The ultrasonic vibrator 11 and the wedge 12 have such a structure that a contacting surface in which a lower portion of the wedge 12 makes contact with an outer pipeline surface 101 of the pipeline 100 is parallel to a surface in which the ultrasonic vibrator 11 is provided on an upper portion of the wedge 12, and ultrasonic waves are vertically emitted to the contacting surface of the outer pipeline surface 101 so as to pass through the outer pipeline surface 101. In order to obviate the presence of air or the like between the outer pipeline surface 101 and the lower portion of the wedge 12 where it is difficult for ultrasonic waves to pass through the air or the like, an ultrasonic connection medium 13 serving as an ultrasonic coupler is provided in the lower portion of the wedge 12. The ultrasonic connection medium 13 is realized by purified water, alcohol, silicon, or the like. The ultrasonic connection medium 13 may be in the form of liquid, gel, rubber, or the like. The ultrasonic vibrator 11, the wedge 12, and the ultrasonic connection medium 13 form an ultrasonic probe 14. Moreover, an ultrasonic absorber 15 that absorbs interference waves transmitted while experiencing multiple reflections through a thick portion of the pipeline 100 is disposed in the outer pipeline surface 101 around the ultrasonic probe 14. The measuring unit 10 includes the ultrasonic probe 14 and the ultrasonic absorber 15.

The main body 20 includes a transmitting unit 21, a receiving unit 22, a switch 23, a time measuring unit 24, a fluid type determining unit 25, a storage unit 26, and an input/output unit 27, and these respective units are connected to a control unit 28. The switch 23 is electrically connected to the ultrasonic vibrator 11.

The transmitting unit 21 generates an ultrasonic transmission pulsating electrical signal for causing the ultrasonic vibrator 11 to generate an ultrasonic signal and outputs the same to the ultrasonic vibrator 11 via the switch 23. The ultrasonic vibrator 11 generates an ultrasonic signal according to the ultrasonic transmission pulsating electrical signal. The generated ultrasonic signal passes through the pipeline 100 via the wedge 12 and enters the fluid 103. The ultrasonic signal entering the fluid 103 is reflected from an inner pipeline surface 102 on a side opposite to the arrangement position of the ultrasonic probe 14, makes one-round trip through the fluid 103, passes through the pipeline 100 again, and then enters the ultrasonic vibrator 11 via the wedge 12. The ultrasonic signal entering the ultrasonic vibrator 11 is converted to an ultrasonic reception pulsating electrical signal by the ultrasonic vibrator 11 and is output to the receiving unit 22. The control unit 28 connects the switch 23 to the transmitting unit 21 during transmission of the ultrasonic transmission pulsating electrical signal only and connects the switch 23 to the receiving unit 22 during reception of the ultrasonic reception pulsating electrical signal after the ultrasonic transmission pulsating electrical signal is transmitted.

The time measuring unit 24 measures a propagation time required for the ultrasonic signal entering the pipeline 100 vertically to make one-round trip through the fluid 103 based on the transmission time (the time at which the ultrasonic signal is transmitted from the ultrasonic vibrator 11) of the ultrasonic transmission pulsating electrical signal transmitted by the transmitting unit 21 and the reception time (the time at which the reflection waves of the ultrasonic signal are received by the ultrasonic vibrator 11) of the ultrasonic reception pulsating electrical signal received by the receiving unit 22.

Figure 2:
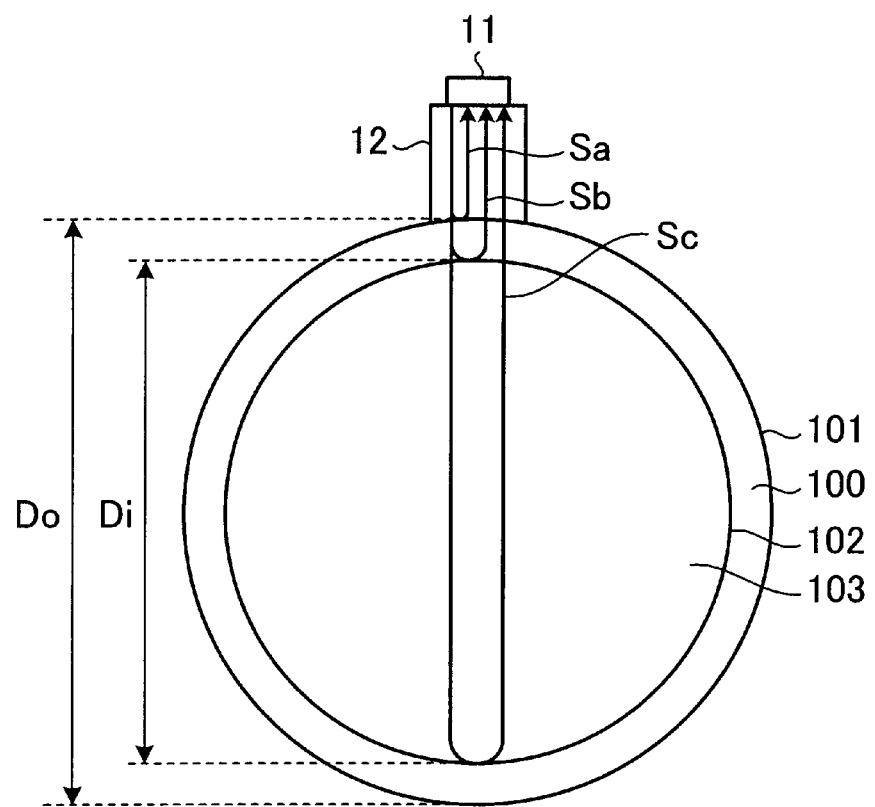
FIG. 2 is a schematic diagram illustrating the state of reflection waves of an ultrasonic signal emitted from an ultrasonic vibrator toward a pipeline.

Here, as illustrated in FIG. 2, the reflection waves of the ultrasonic signal output from the ultrasonic vibrator 11 come in three types Sa, Sb, and Sc. Reflection waves Sa are waves of some the ultrasonic signals emitted from the ultrasonic vibrator 11, with these waves returning to the ultrasonic vibrator 11 after being reflected from the interface between the wedge 12 and the outer pipeline surface 101. Reflection waves Sb are waves of some of the ultrasonic signals having passed through the interface between the wedge 12 and the outer pipeline surface 101, with these waves returning to the ultrasonic vibrator 11 after being reflected from the interface between the inner pipeline surface 102 and the fluid 103. Reflection waves Sc are waves that return to the ultrasonic vibrator 11 after passing through the fluid 103, being reflected from the inner pipeline surface 102 on the opposite side, making one-round trip through the fluid 103, and passing through the pipeline 100 and the wedge 12 among the ultrasonic signals having passed through the interface between the inner pipeline surface 102 and the fluid 103.

Figure 3:
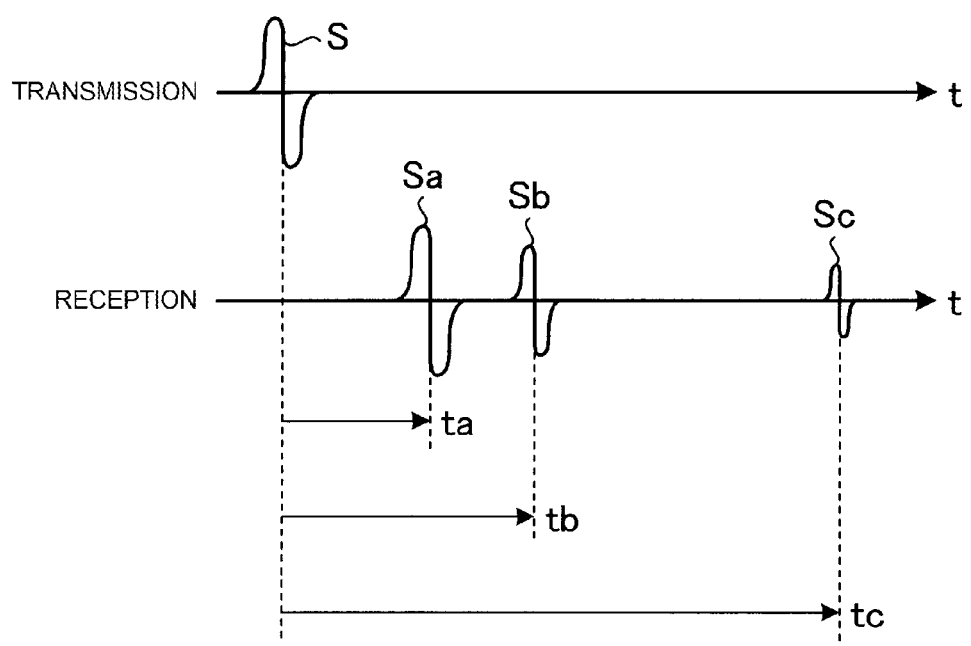
FIG. 3 is a timing chart illustrating the timings at which the ultrasonic vibrator receives reflection waves of an ultrasonic signal transmitted by the ultrasonic vibrator.

FIG. 3 is a timing chart illustrating the timings at which the ultrasonic vibrator 11 receives the reflection waves Sa, Sb, and Sc of the ultrasonic signal S transmitted by the ultrasonic vibrator 11. As illustrated in FIG. 3, time ta is the time (third time) elapsed from transmission of the ultrasonic signal S transmitted by the ultrasonic vibrator 11 to reception of the reflection waves Sa. Time tb is the time (first time) elapsed from transmission of the ultrasonic signal S transmitted by the ultrasonic vibrator 11 to reception of the reflection waves Sb. Time tc is the time (second time) elapsed from transmission of the ultrasonic signal S transmitted by the ultrasonic vibrator 11 to reception of the reflection waves Sc.

As described above, the time measuring unit 24 calculates a propagation time tf required for the ultrasonic signal entering the pipeline 100 vertically to make one-round trip through the fluid 103 according to Equation (1), $$tf = tc - tb \qquad (1).$$

Fluid Type Determination when Inner Pipeline Diameter Di is Known—

The fluid type determining unit 25 calculates the velocity of sound in the fluid 103 by dividing twice the inner pipeline diameter Di by the propagation time tf calculated by the time measuring unit 24. Here, the storage unit 26 stores velocity of sound-to-fluid type relation information DT1. The velocity of sound-to-fluid type relation information DT1 indicates a relation between a fluid type and the velocity of sound uniquely determined by the type of a fluid. For example, when the fluid type is town gas, the town gas contains methane as its main component and the velocity of sound therein is approximately 430 m/s. Moreover, when the fluid type is water, the velocity of sound therein is approximately 1500 m/s. Moreover, when the fluid type is air, the velocity of sound therein is approximately 340 m/s. On the other hand, the inner pipeline diameter Di is a known value input from the input/output unit 27. The inner pipeline diameter Di and outer pipeline diameter Do of the pipeline 100 buried under the ground are specified in the JIS standards and the like, and the inner pipeline diameter Di can be known upon reading the standard information written on the outer surface of the measuring target pipeline 100. That is, the fluid type determining unit 25 calculates the velocity of sound in the fluid 103 by dividing twice the inner pipeline diameter Di by the propagation time tf and determines the fluid type corresponding to the calculated velocity of sound by referring to the velocity of sound-to-fluid type relation information DT1. The control unit 28 outputs the fluid type determined by the fluid type determining unit 25 from the input/output unit 27.

Fluid Type Determination when Inner Pipeline Diameter Di is Unknown—

On the other hand, in old pipelines and buried pipelines, it may sometimes be difficult to read or identify pipe specification information written on the pipelines because the section showing the information is worn or buried. Moreover, some pipelines may not have the standard information. In such a case, the fluid type determining unit 25 estimates the inner pipeline diameter Di using the time ta (third time), the outer pipeline diameter Do, and the pipeline material. As long as the inner pipeline diameter Di can be estimated, the fluid type determining unit 25 can perform the fluid type determining process in a manner similarly to when the inner pipeline diameter Di is known.

The outer pipeline diameter Do can be measured by digging the ground so that about half of the pipeline 100 appears. Moreover, the pipeline material of the pipeline 100 can be determined by its appearance. The outer pipeline diameter Do and the pipeline material are input from the input/output unit 27.

The fluid type determining unit 25 calculates the velocity of sound in the pipeline 100 corresponding to the input pipeline material based on pipeline material-to-velocity of sound relation information DT2 stored in advance in the storage unit 26. For example, the velocity of sound is approximately 6000 m/s when the pipeline material is metal such as iron or stainless steel, the velocity of sound is approximately 2300 m/s when the pipeline material is polyvinyl chloride which is plastic, and the velocity of sound is approximately 1900 m/s when the pipeline material is polyethylene which is plastic. It is easy to visually determine whether the pipeline material is metal or plastic. Thus, in the pipeline material-to-velocity of sound relation information DT2, the velocity of sound Cp is stored as 6000 m/s for the pipeline 100 when the pipeline material is metal, and the velocity of sound Cp is stored as 2000 m/s for the pipeline 100 when the pipeline material is plastic.

The fluid type determining unit 25 calculates the inner pipeline diameter Di using the outer pipeline diameter Do, the velocity of sound Cp in the pipeline 100, the time tb, and the time ta according to Equation (2) below, $$Di = Do - Cp(tb - ta) \qquad (2).$$

Here, the value of Cp(tb−ta) corresponds to twice the thickness of the pipeline 100.

However, since the velocity of sound Cp in the pipeline 100 is estimated, the value of the inner pipeline diameter Di in Equation (2) has an error. However, if the thickness of the pipeline 100 is estimated from the outer pipeline diameter Do, for example, when the diameter is 50 A (50 mm), the thickness of a metal pipeline ranges between 1.5 mm and 9 mm and the thickness of a plastic pipeline ranges between 2 mm and 8 mm. Thus, a thickness deviation is large and the error increases. On the other hand, in relation to a deviation in the velocity of sound Cp in the pipeline 100 depending on a difference in the pipeline material, it is possible to determine visually whether the pipeline material is metal or plastic. Thus, the thickness can be estimated with high accuracy by estimating the velocity of sound Cp in the pipeline 100 as described above. As a result, in the first embodiment, the inner pipeline diameter Di can be calculated with high accuracy.

Fluid Type Determining Process—

Figure 4:
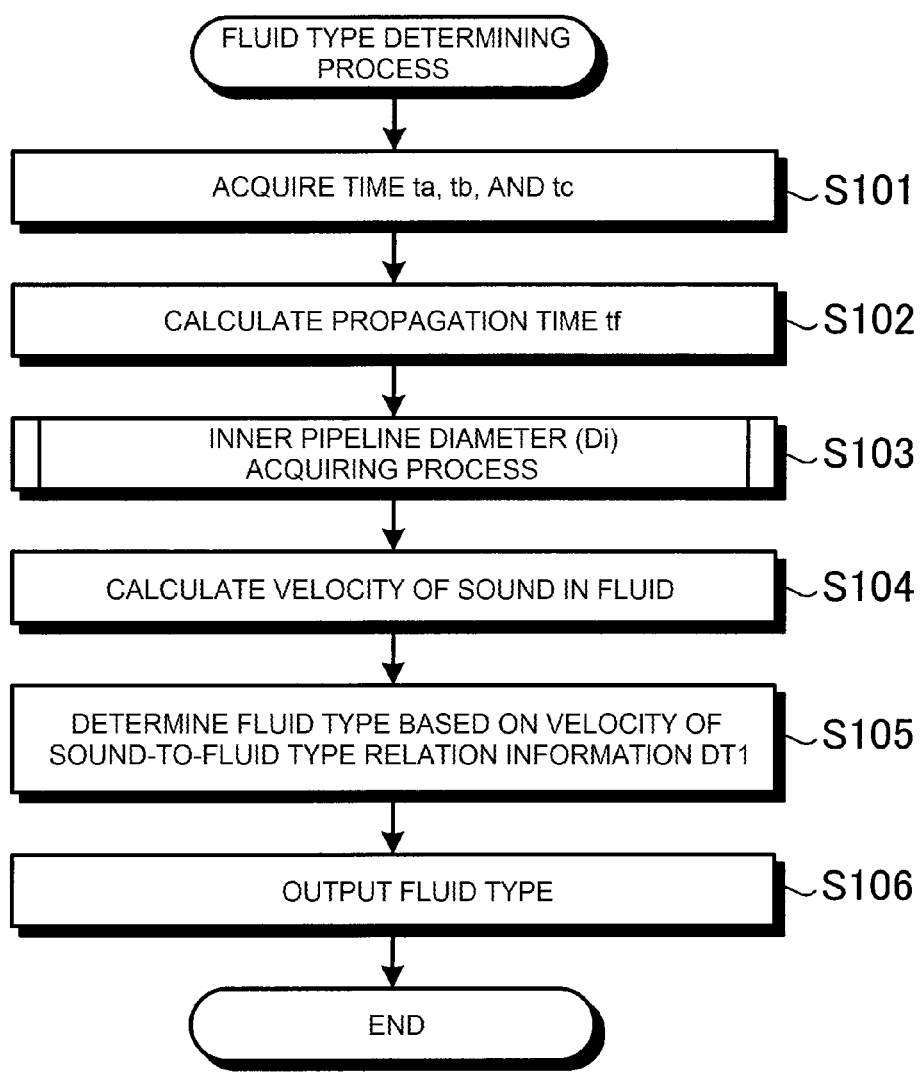
FIG. 4 is a flowchart illustrating the flow of a fluid type determining process performed by a fluid type determining unit.

Here, the flow of a fluid type determining process performed by the fluid type determining unit 25 will be described with reference to the flowcharts illustrated in FIGS. 4 and 5. First, as illustrated in FIG. 4, the fluid type determining unit 25 acquires the time ta, tb, and tc from the time measuring unit 24 (step S101). After that, the propagation time tf is calculated according to Equation (1) (step S102). After that, an inner pipeline diameter (Di) acquiring process of acquiring the inner pipeline diameter Di input by the input/output unit 27 or the inner pipeline diameter Di calculated according to Equation (2) is performed (step S103).

After that, the fluid type determining unit 25 calculates the velocity of sound of the fluid 103 by dividing twice the inner pipeline diameter Di by the propagation time tf (step S104). Further, the fluid type determining unit 25 determines the fluid type corresponding to the calculated velocity of sound using the velocity of sound-to-fluid type relation information DT1 (step S105) and outputs the fluid type from the input/output unit 27 (step S106). In this way, this process ends.

Figure 5:
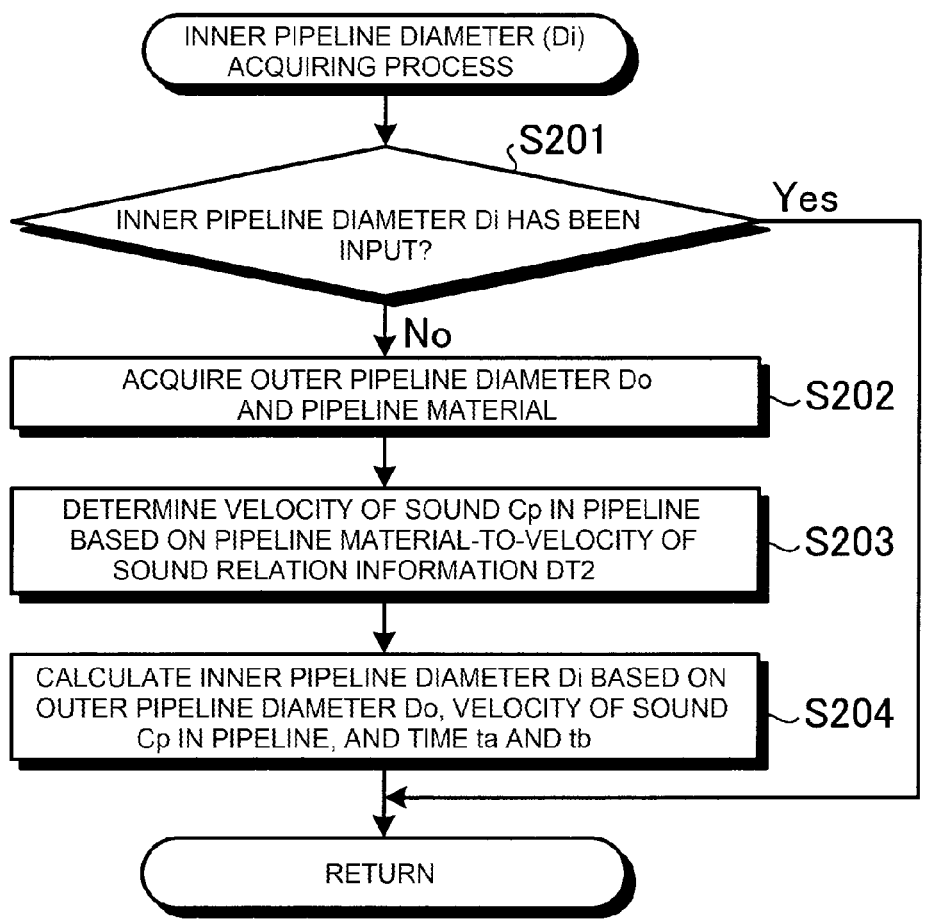
FIG. 5 is a detailed flowchart illustrating the flow of an inner pipeline diameter acquiring process.

FIG. 5 is a detailed flowchart illustrating the flow of the inner pipeline diameter (Di) acquiring process illustrated in step S103. As illustrated in FIG. 5, first, the fluid type determining unit 25 determines whether the inner pipeline diameter Di has been input by the input/output unit 27 (step S201). When the inner pipeline diameter Di has been input (step S201: Yes), the flow returns to step S103 with no modification.

On the other hand, when the inner pipeline diameter Di has not been input (step S201: No), the outer pipeline diameter Do and the pipeline material input from the input/output unit 27 are acquired (step S202). After that, the fluid type determining unit 25 determines the velocity of sound Cp in the pipeline 100 corresponding to the acquired pipeline material based on the pipeline material-to-velocity of sound relation information DT2 (step S203). After that, the fluid type determining unit 25 calculates the inner pipeline diameter Di using Equation (2) (step S204), and the flow returns to step S103.

Structure of Ultrasonic Probe—

Figure 6:
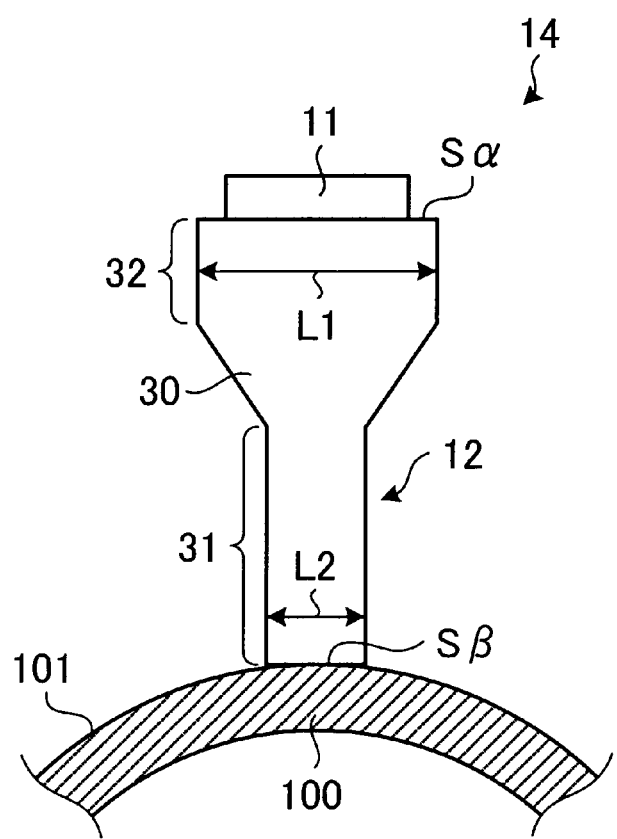
FIG. 6 is a diagram illustrating the structure of an ultrasonic probe when seen from a surface vertical to an axial direction of a pipeline.
Figure 7:
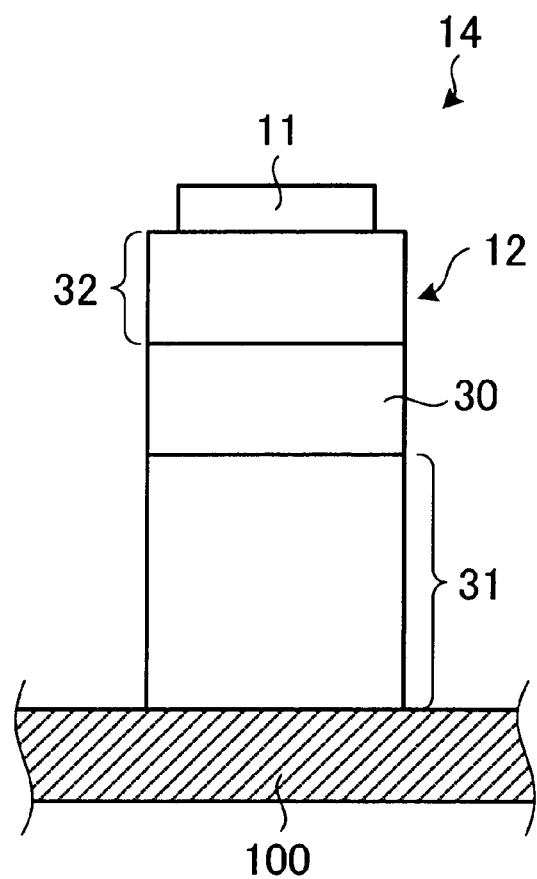
FIG. 7 is a diagram illustrating the structure of the ultrasonic probe when seen from a surface horizontal to the axial direction of the pipeline.

FIG. 6 is a diagram illustrating the structure of the ultrasonic probe 14 when seen from the surface vertical to the axial direction of the pipeline 100. Moreover, FIG. 7 is a diagram illustrating the structure of the ultrasonic probe 14 when seen from the surface horizontal to the axial direction of the pipeline 100. As illustrated in FIGS. 6 and 7, a side surface (the surface extending in the direction vertical to the axial direction of the pipeline 100) of the wedge 12 has an inclined surface portion 30 that is inclined at an angle with respect to a line perpendicular to a pipeline contacting surface Sβ. Moreover, a length L1 in the cross-section, of a vibrator surface Sα of the wedge 12 on which the ultrasonic vibrator 11 is disposed is smaller than a length L2 in the cross-section, of the pipeline contacting surface Sβ.

In the ultrasonic probe 14, ultrasonic waves are generated on approximately the entire surface of the ultrasonic vibrator 11 and propagate in the direction vertical to the pipeline 100. The ultrasonic waves entering the inclined surface portion 30 being in the propagation path are reflected and collected and finally enter the pipeline 100 while concentrating on the pipeline contacting surface Sβ that is narrower than the vibrator surface Sα.

Figure 8:
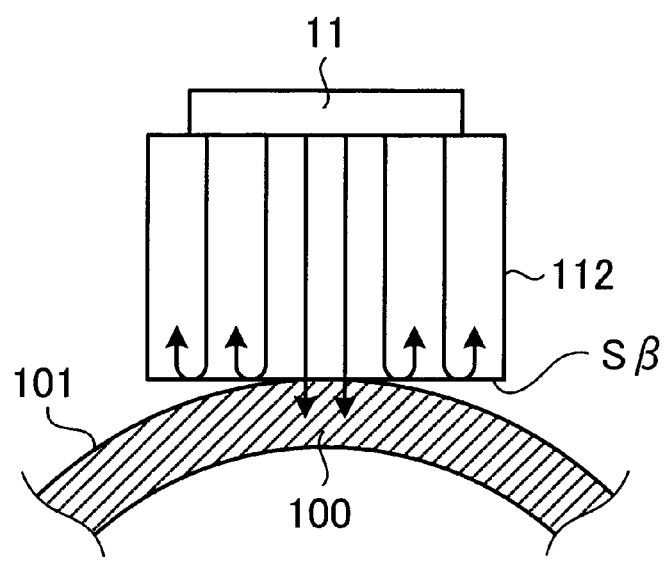
FIG. 8 is a diagram illustrating the structure of a wedge of a conventional ultrasonic probe.

Here, a wedge 112 of a conventional ultrasonic probe illustrated in FIG. 8 does not have the inclined surface portion 30. Thus, as illustrated in FIG. 8, a large part of the ultrasonic waves generated by the ultrasonic vibrator 11 are reflected from the space between the outer pipeline surface 101 which is a curved surface and the pipeline contacting surface Sβ of the wedge 112, which is a flat surface, and do not enter the pipeline 100. Thus, ultrasonic waves do not enter the pipeline 100 efficiently.

In contrast, in the first embodiment, ultrasonic waves can pass and enter the pipeline 100 while concentrating on the pipeline contacting surface Sβ which has a small area and makes contact with the outer pipeline surface 101 which is a curved surface. Thus, ultrasonic waves can enter the pipeline 100 efficiently. As a result, even when ultrasonic waves pass through a fluid such as gas or vapor, through which it is difficult for ultrasonic waves to pass, or even when the pipeline 100 is old, rusty, or corroded, or has sediments adhering thereto and it is difficult for ultrasonic waves to pass through the pipeline, since high intensity ultrasonic waves can enter the pipeline 100, it is possible to measure ultrasonic waves with high accuracy in the fluid 103.

In the first embodiment, since the stress applied when installing the ultrasonic probe 14 on the pipeline 100 concentrates on the narrow pipeline contacting surface Sβ, the outer pipeline surface 101 and the wedge 12 adhere further closely, and this close adhesion further improves the transmission efficiency of ultrasonic waves.

Moreover, although the inclined surface portion 30 is configured as a flat surface, the inclined surface portion 30 is not limited to a flat surface as long as the inclined surface portion 30 has such a shape in a side view that the pipeline contacting surface Sβ is smaller than the vibrator surface Sα.

When Transmission and Reception Ultrasonic Vibrators are Mounted on One Wedge—

Figure 9:
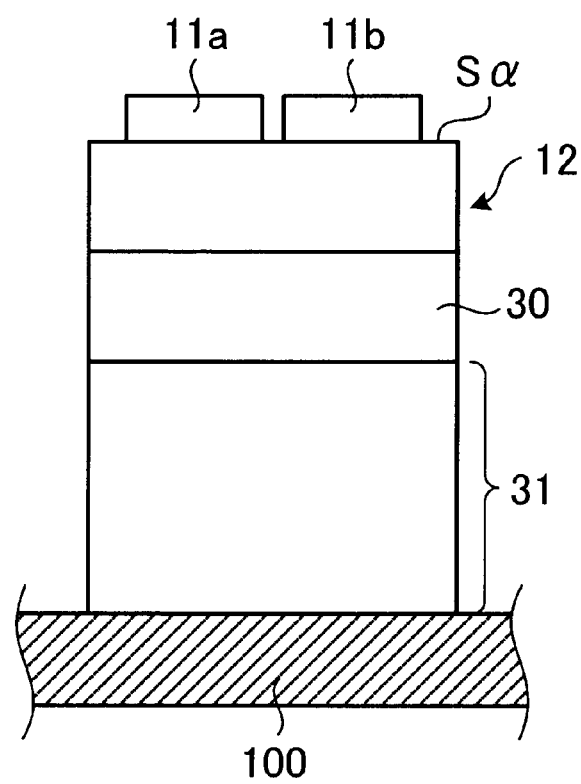
FIG. 9 is a diagram illustrating an example of an ultrasonic probe in which two ultrasonic vibrators are provided on a vibrator surface of one wedge.

Further, in FIGS. 6 and 7, although one transceiving ultrasonic vibrator 11 is provided on the vibrator surface Sα of one wedge 12, two ultrasonic vibrators 11a and 11b may be provided on the vibrator surface Sα of one wedge 12 as illustrated in FIG. 9. One ultrasonic vibrator 11a is used as a transmission ultrasonic vibrator, and the other ultrasonic vibrator 11b is used as a reception ultrasonic vibrator. In this case, the ultrasonic vibrators 11a and 11b are arranged to be adjacent to each other in the axial direction of the pipeline 100. In general, when an electrical signal is transmitted to an ultrasonic vibrator to generate ultrasonic waves, echo noise occurs in a piezoelectric element and a circuit or between the piezoelectric element and the circuit, and it may take time until the echo noise is attenuated. When the pipeline diameter is small, for example, reception ultrasonic waves may enter the ultrasonic vibrator before the echo noise is attenuated, which disturbs measurement of the propagation time. In contrast, as illustrated in FIG. 9, when the transmission ultrasonic vibrator and the reception ultrasonic vibrator are provided separately, echo noise occurs between the transmission ultrasonic vibrator and a transmission circuit and has no influence on the reception ultrasonic vibrator and a reception circuit.

Wedge Material—

However, a piezoelectric element is generally used as the ultrasonic vibrator 11. The piezoelectric element has a Curie point and the use under high temperature is limited. In contrast, in the first embodiment, an intermediate portion 31 is provided between the inclined surface portion 30 and the pipeline contacting surface Sβ so that the inclined surface portion 30 and the pipeline contacting surface Sβ are separated so as not to be connected directly. As a result, since the intermediate portion 31 has a narrow shape in relation to an intermediate portion 32 disposed between the inclined surface portion 30 and the vibrator surface Sα, it is possible to increase a heat-radiating effect. Thus, by adjusting the length of the intermediate portion 31 appropriately, the heat of the pipeline 100 is radiated to the surrounding and is rarely transmitted to the ultrasonic vibrator 11. As a result, the device of the first embodiment can measure a high-temperature fluid easily. Similarly, the device can measure a low-temperature fluid easily.

Figure 10:
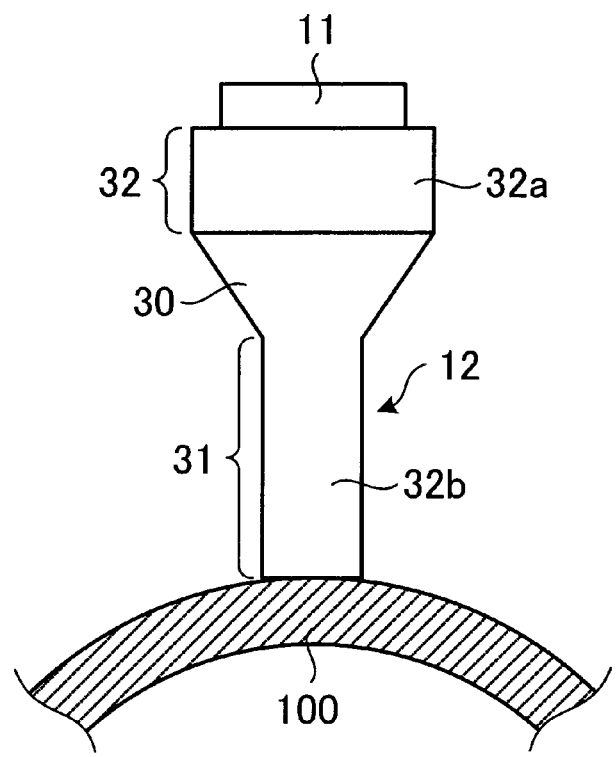
FIG. 10 is a diagram illustrating an example of an ultrasonic probe in which an inclined surface portion and a lower intermediate portion are formed of metal and an upper intermediate portion is formed of a resin.
Figure 11:
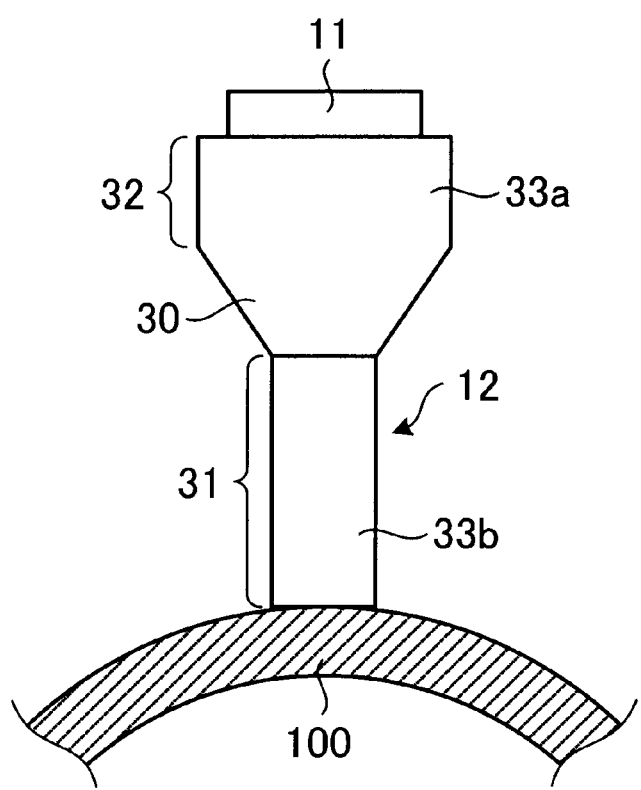
FIG. 11 is a diagram illustrating an example of an ultrasonic probe in which a lower intermediate portion is formed of metal and an upper intermediate portion and an inclined surface portion are formed of a resin.

Further, as illustrated in FIGS. 10 and 11, the wedge 12 is preferably formed of a combination of a plurality of materials. For example, a portion closer to the pipeline 100 may be formed as a metal member having high heat resistance since the portion is heated easily. A portion closer to the ultrasonic vibrator 11 may be formed as a resin material in order to improve assembling properties such as adhesion properties since the portion is cooled by heat radiation. In this way, it is possible to meet high-temperature applicability and satisfactory assembling properties. Specifically, in FIG. 10, the portion having the inclined surface portion 30 and the intermediate portion 31 are formed as a metal member 32b and the intermediate portion 32 is formed as a resin member 32a. Moreover, in FIG. 11, the intermediate portion 31 is formed as a metal member 33b and the intermediate portion 32 and the portion having the inclined surface portion 30 are formed as a resin member 33a.

Angle of Inclined Surface Portion—

Figure 12:
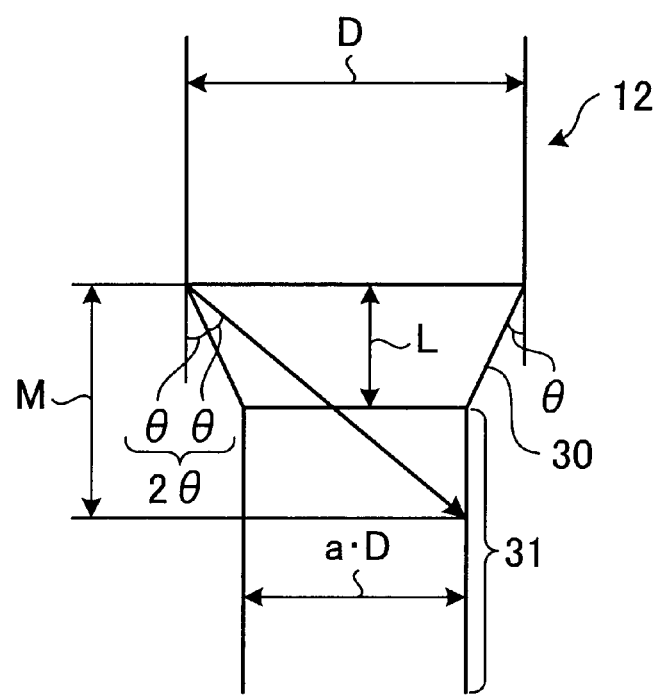
FIG. 12 is an explanatory diagram for describing a limitation on the angle θ when the wedge has a structure that is bilaterally symmetrical in a surface vertical to the axial direction of the pipeline.

However, there is a limit on the angle θ between the inclined surface portion 30 and the line perpendicular to the pipeline contacting surface Sβ. As illustrated in FIG. 12, this limitation on the angle θ will be described by way of an example in which the wedge 12 has a structure that is bilaterally symmetrical in a surface vertical to the axial direction of the pipeline 100. Here, it is assumed that the length in the cross-section, of the vibrator surface Sα is D and the length in the cross-section, of the pipeline contacting surface Sβ is a×D. However, "a" is a value in the range of 0<a<1.

Figure 13:
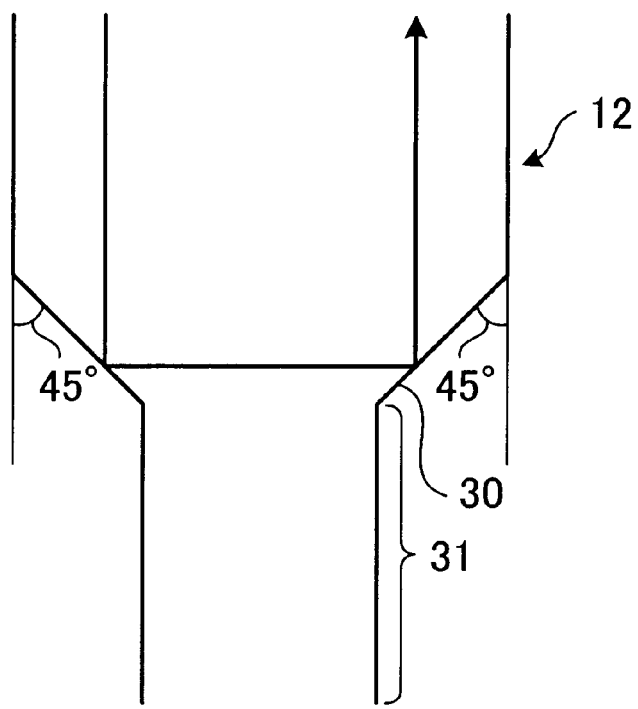
FIG. 13 is an explanatory diagram illustrating the locus of ultrasonic waves reflected from an inclined surface portion when the angle θ is 45°.

First, as illustrated in FIG. 13, when the angle θ is 45°, the ultrasonic waves reflected from the inclined surface portion 30 travel horizontally to the pipeline 100 and are reflected again from the inclined surface portion 30 on the opposite side and return to the ultrasonic vibrator 11. In this case, it is difficult to allow ultrasonic waves to enter the pipeline 100 in a concentrated manner.

Thus, it is necessary to allow the ultrasonic waves reflected from the inclined surface portion 30 to enter the pipeline 100 in a concentrated manner without being reflected from the inclined surface portion 30 on the opposite side. It is assumed that the length of a component of the inclined surface portion 30 vertical to the pipeline is L, and the length of a component vertical to the pipeline 100, corresponding to the distance in which the ultrasonic waves reflected from the inclined surface portion 30 reaches the intermediate portion 31 between the pipeline contacting surface Sβ and the inclined surface portion 30 on the opposite side is M. The condition under which the ultrasonic waves reflected from the inclined surface portion 30 are not reflected from the inclined surface portion 30 on the opposite side is expressed by Equation (3), $$M > L \quad (3).$$

The most strict condition that satisfies Equation (3) is obtained when ultrasonic waves are reflected from the outermost side of the inclined surface portion 30 (that is, the portion closest to the vibrator surface Sα), and in that case, the lengths L and M are expressed by Equations (4) and (5), $$L \cdot \tan \theta = (D - a \cdot D)/2 \quad (4),$$

$$M \cdot \tan 2\theta = (D + a \cdot D)/2 \quad (5).$$

When Equations (4) and (5) are substituted into Equation (3), D is eliminated, and Equation (6) is obtained, $$\tan 2\theta / \tan \theta < (1+a)/(1-a) \quad (6).$$

When a wedge shape that satisfies Equation (6) is designed, ultrasonic waves can be concentrated on the pipeline contacting surface Sβ.

When the angle θ in Equation (6) approaches "0," since tan θ approximates to θ, the value "a" decreases and ultrasonic waves can be concentrated further. However, the value "a" is never smaller than ⅓. Thus, when the wedge 12 is designed, the value "a" needs to be larger than ⅓. As a result, the value "a" needs to be designed to be in the range of ⅓<a<1. Moreover, if the angle θ is 45°, since 2θ becomes 90° and tan 2θ becomes infinite, the angle θ cannot be designed to be at 45° or larger. Therefore, the angle θ needs to be designed to be in the range of 0°<θ<45°.

Ultrasonic Absorber—

Figure 14:
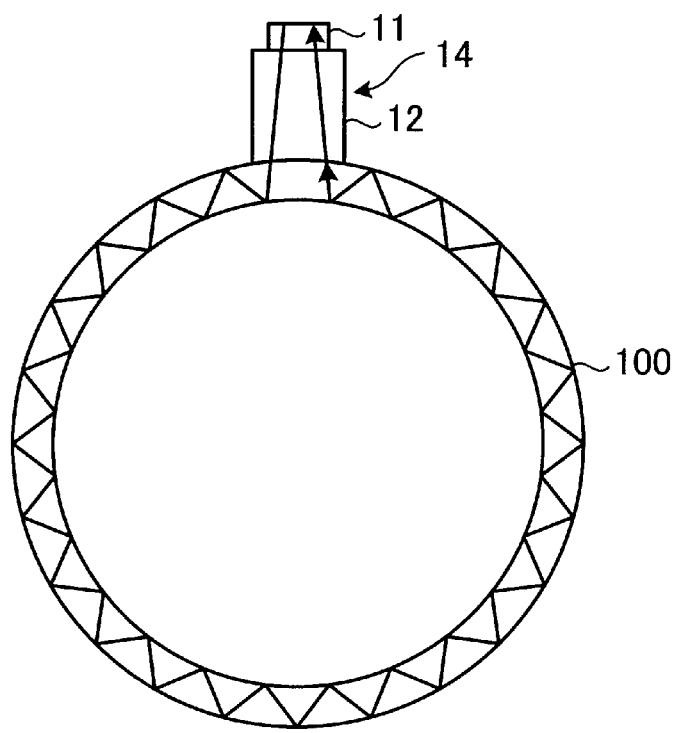
FIG. 14 is a schematic diagram illustrating an example of interference waves transmitted while experiencing multiple reflections in the pipeline.
Figure 15:
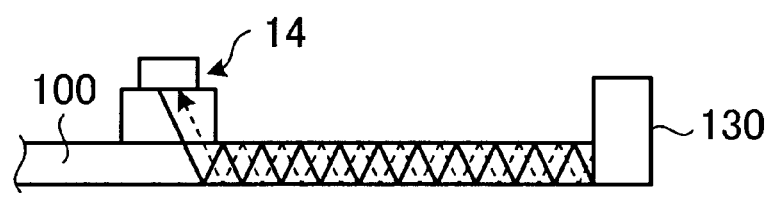
FIG. 15 is a schematic diagram illustrating an example of interference waves reflected from a flange after experiencing multiple reflections in the pipeline.
Figure 15:
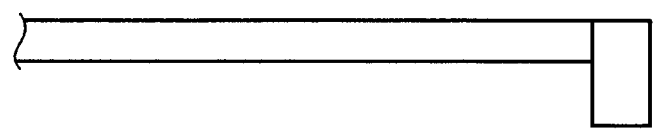

However, some of the ultrasonic signals entering from the contacting surface between the wedge 12 and the outer pipeline surface 101 are transmitted while experiencing multiple reflections using the inside of the pipeline 100 as a waveguide. For example, as illustrated in FIG. 14, interference waves transmitted through the pipeline 100 while experiencing multiple reflections may return to the ultrasonic vibrator 11 after making multiple round-trips through the pipeline 100. FIG. 15 is a vertical cross-sectional view of the pipeline 100. As illustrated in FIG. 15, interference waves transmitted through the pipeline 100 may be reflected from the flange 130 provided at the end or the like in the axial direction of the pipeline 100 and may return to the ultrasonic vibrator 11. In FIG. 15, an outbound ultrasonic signal is depicted by a solid line, and an incoming ultrasonic signal returning to the ultrasonic vibrator 11 after being reflected from the flange 130 is depicted by a broken line. These interference waves cause a measurement error in the time tc when the interference waves overlap the reflection waves Sc illustrated in FIG. 3 on the time axis or occur near the reception time of the reflection waves Sc.

Figure 16:
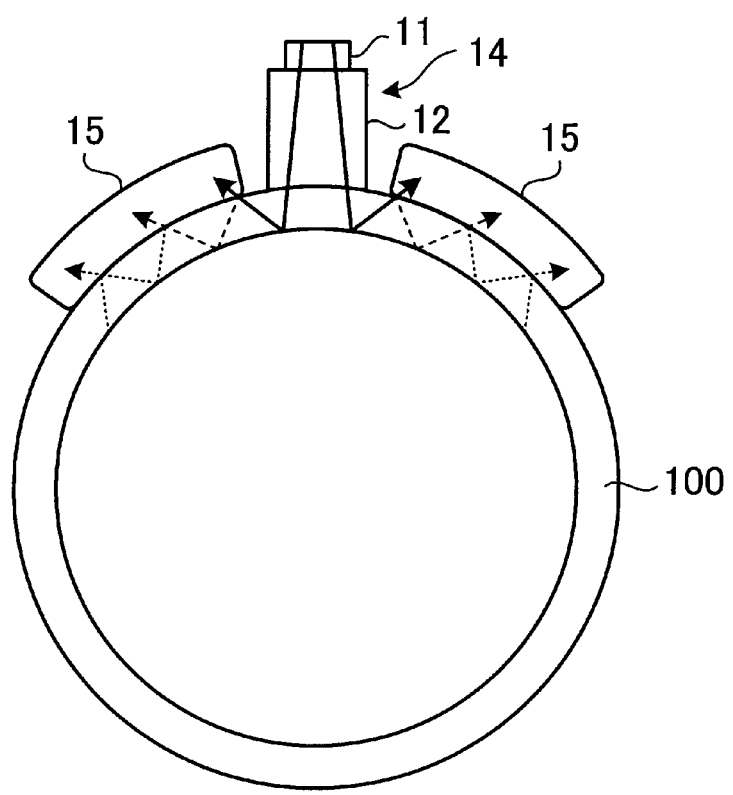
FIG. 16 is a schematic diagram illustrating a state in which interference waves transmitted while experiencing multiple reflections in the pipeline are attenuated by an ultrasonic absorber.

Thus, as illustrated in FIGS. 1 and 16, the ultrasonic absorber 15 is provided on the surface of the outer pipeline surface 101 near the ultrasonic probe 14. A base material of the ultrasonic absorber 15 is formed of a substance such as rubber or clay that attenuates ultrasonic waves. As illustrated in FIG. 16, when interference waves experience multiple reflections through the pipeline 100, some of the interference waves pass through the ultrasonic absorber 15 and disappear by being attenuated in the ultrasonic absorber 15. Thus, a large part of the interference waves become extinct in the course of passing through the pipeline portion with which the ultrasonic absorber 15 and the outer pipeline surface 101 make contact. Due to this, it is possible to suppress a measurement error in the reflection waves Sc occurring due to overlap or presence of interference waves at the reception time of the reflection waves Sc. The ultrasonic absorber 15 is preferably disposed in the axial direction of the pipeline 100 as well as the circumferential direction of the pipeline 100 so as to surround all sides of the ultrasonic probe 14. In this way, it is possible to absorb interference waves reflected from the flange 130 illustrated in FIG. 15.

Figure 17:
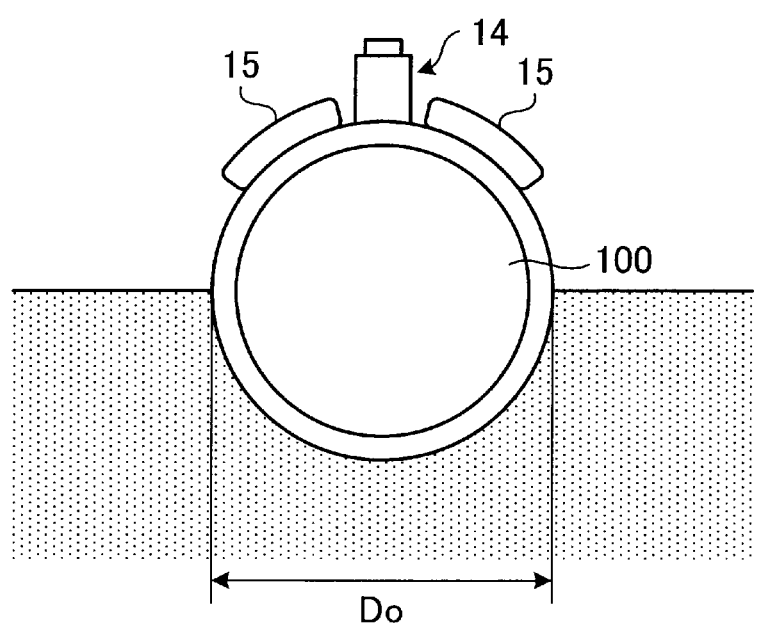
FIG. 17 is a schematic diagram illustrating an example in which an ultrasonic absorber is provided so as to cover a range of regions corresponding to half or smaller of the circumference of the pipeline.

As illustrated in FIG. 17, the ultrasonic absorber 15 preferably covers a range of regions corresponding to half or smaller of the circumference of the pipeline 100. In this case, when the ground is dug so that about half of the pipeline 100 appears, it is possible to measure the outer pipeline diameter Do, install the ultrasonic absorber 15, and install the measuring unit 10 easily.

When the pipeline 100 is metal, it is preferable to mix tungsten particles into the base material such as rubber or clay, of the ultrasonic absorber 15 to thereby increase the specific gravity to increase an interference wave absorbing effect. This is because, when the pipeline 100 and the ultrasonic absorber 15 have similar specific gravity, the proportion of the interference waves passing through the ultrasonic absorber 15 increases and the ultrasonic wave absorbing effect can be increased. In general, the specific gravity of rubber or clay which is the base material of the ultrasonic absorber 15 is approximate 1 to 2, which is far different from the specific gravity which is approximately 8, of a metal pipeline. Thus, by mixing tungsten whose specific gravity is approximately 19, the specific gravity of the ultrasonic absorber 15 can be made similar to that of the metal pipeline.

Further, when the pipeline 100 is formed of a magnetic substance such as iron or steel, it is preferable to mix a magnetic substance into the ultrasonic absorber 15, process the ultrasonic absorber 15 in a sheet form, and magnetize the sheet to obtain a magnet sheet. When the ultrasonic absorber 15 is processed in a sheet form, the ultrasonic absorber 15 can be easily installed in the pipeline 100. Moreover, when iron is used as the magnetic substance, since the iron has a specific gravity as small as 8, it is preferable to mix tungsten having a large specific gravity together.

In the first embodiment described above, an ultrasonic signal is incident vertically to the outer pipeline surface 101 of the pipeline 100 from one ultrasonic probe 14, and the inclined surface portion 30 is provided so that the ultrasonic signal emitted from the ultrasonic vibrator 11 is concentrated and a highly dense ultrasonic signal enters the pipeline 100. Thus, it is possible to measure fluid characteristics such as a fluid type in various types of pipelines with an easy-to-install structure without breaking the pipeline 100. In particular, the ultrasonic signal can efficiently pass through the pipeline 100 having a curved outer surface. Thus, even when ultrasonic waves pass through a fluid such as gas or vapor, through which it is difficult for ultrasonic waves to pass, or even when the pipeline is old, rusty, or corroded, or has sediments adhering thereto and it is difficult for ultrasonic waves to pass through the pipeline, it is possible to measure ultrasonic waves with high accuracy.

Moreover, since the ultrasonic vibrator 11 that is vulnerable to high temperature can be separated from the pipeline 100, it is possible to measure hot and cool fluid easily.

Further, since the ultrasonic absorber 15 can reduce interference waves returning while experiencing multiple reflections through the pipeline 100, it is possible to suppress the influence of interference waves and to measure an accurate propagation time.

Second Embodiment—Entire Configuration

Figure 18:
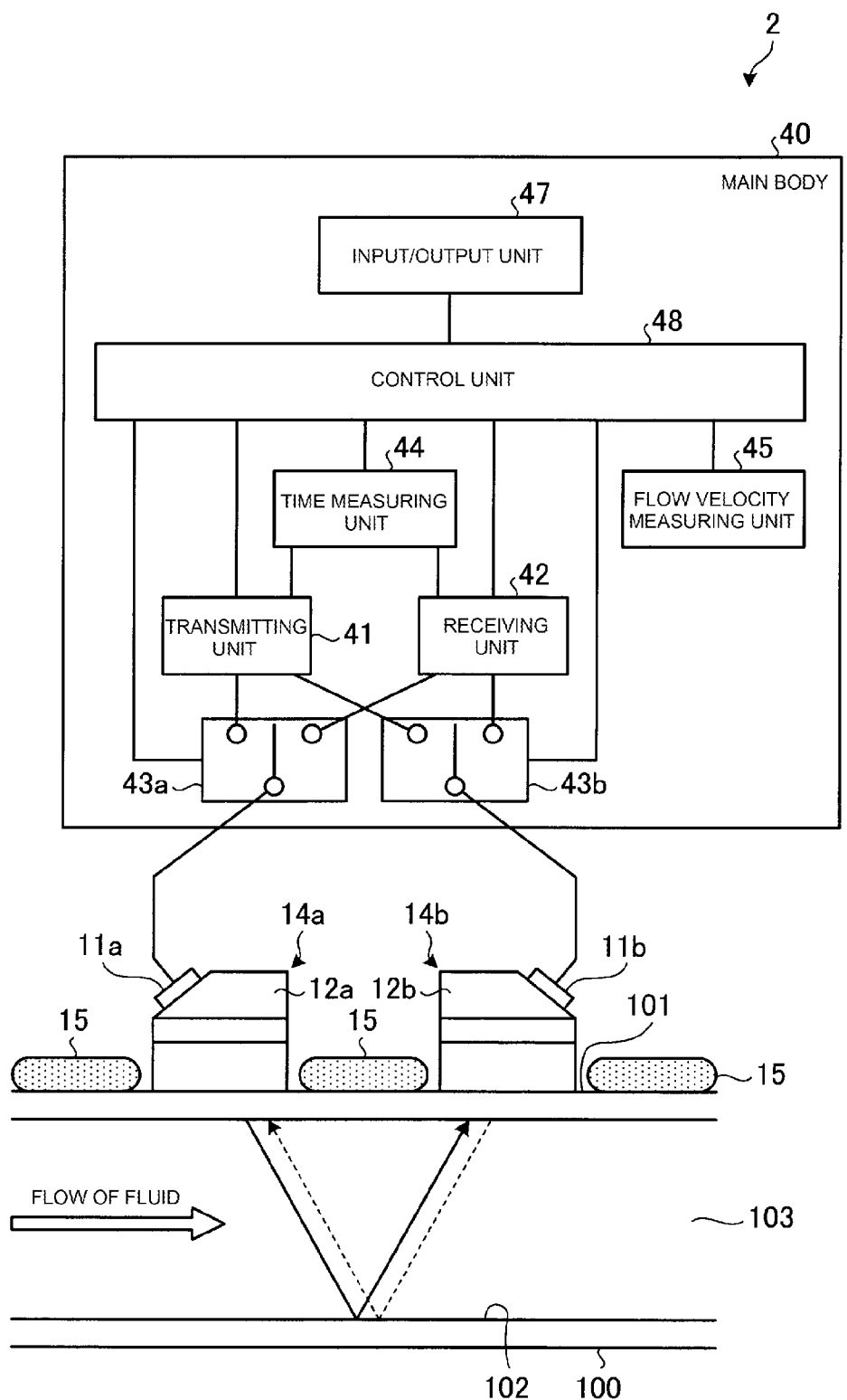
FIG. 18 is a schematic diagram illustrating an entire configuration of a fluid measuring device according to a second embodiment of the present invention.

FIG. 18 is a schematic diagram illustrating an entire configuration of a fluid measuring device according to a second embodiment of the present invention. In FIG. 18, a fluid measuring device 2 measures the velocity of a fluid 103 flowing through a pipeline 100. The type of the fluid 103 may be determined based on the propagation time measured in the same manner as the first embodiment.

In the fluid measuring device 2, a plurality of ultrasonic probes 14a and 14b is provided on an outer pipeline surface 101 of the pipeline 100. Here, a pipeline contacting surface of each of wedges 12a and 12b contacting the outer pipeline surface 101 is inclined with respect to a vibrator surface on which each of ultrasonic vibrators 11a and 11b is provided, and ultrasonic waves pass obliquely through the outer pipeline surface 101.

The ultrasonic vibrators 11a and 11b are connected to switches 43a and 43b of a main body 40, respectively. Moreover, the switches 43a and 43b are connected to both a transmitting unit 41 and a receiving unit 42. In FIG. 18, the ultrasonic probe 14a is disposed upstream the flow of the fluid 103, and the ultrasonic probe 14b is disposed downstream the flow of the fluid 103. The switches 43a and 43b are controlled by a control unit 48 so that, when one ultrasonic vibrator is connected to the transmitting unit 41, the other ultrasonic vibrator is connected to the receiving unit 42.

The transmitting unit 41 transmits an ultrasonic transmission pulsating electrical signal to one ultrasonic vibrator 11a to generate ultrasonic waves. The generated ultrasonic waves pass through the wedge 12a and the outer pipeline surface 101 and enter the fluid 103 in the pipeline 100 obliquely. The ultrasonic waves entering the fluid 103 in the pipeline 100 are reflected from an inner pipeline surface 102 on the opposite side, make one-round trip through the fluid 103 obliquely, pass through the outer pipeline surface 101 and the wedge 12b, and enter the other ultrasonic vibrator 11b. The other ultrasonic vibrator 11b converts the entering ultrasonic waves to an ultrasonic reception pulsating electrical signal. Since the other ultrasonic vibrator 11b is connected to the receiving unit 42 by the switch 43b, the converted ultrasonic reception pulsating electrical signal is received by the receiving unit 42.

The time measuring unit 44 measures the propagation time tf from transmission and reception of ultrasonic waves similarly to the first embodiment. Here, a fluid type determining unit 25 and an input/output unit 47 are provided similarly to the first embodiment. Thus, it is possible to calculate the velocity of sound in the fluid 103 and to determine the fluid type based on the velocity of sound. In the second embodiment, the velocity of the fluid 103 is measured.

In this case, by switching the switches 43a and 43b, the time measuring unit 44 measures the propagation time tu from the upstream ultrasonic vibrator 11a to the downstream ultrasonic vibrator 11b in relation to the flow of the fluid 103 and the reverse propagation time td from the downstream ultrasonic vibrator 11b to the upstream ultrasonic vibrator 11a. The ultrasonic wave propagation time changes depending on the carrying effect of the fluid 103 such that the propagation time tu decreases and the propagation time td increases. This difference in the propagation time tu and td changes depending on the velocity of fluid. The flow velocity measuring unit 45 measures this difference to measure the velocity of the fluid 103. When the flow velocity measuring unit 45 calculates the velocity of sound in the fluid 103 using the average of the propagation time tu and td, it is possible to improve the calculation accuracy.

Structure of Ultrasonic Probe—

Figure 19:
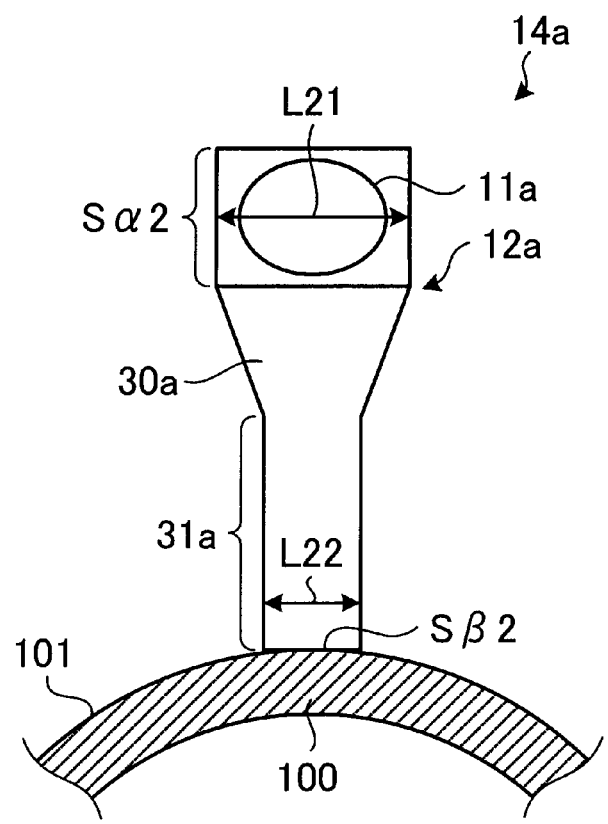
FIG. 19 is a diagram illustrating the structure of an ultrasonic probe according to the second embodiment of the present invention when seen from a surface vertical to an axial direction of a pipeline.
Figure 20:
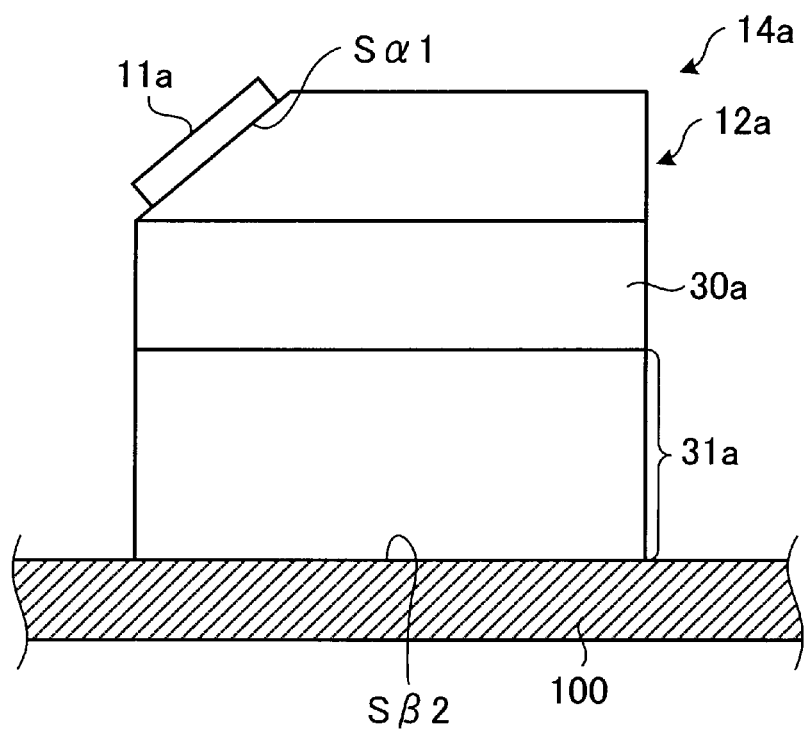
FIG. 20 is a diagram illustrating the structure of the ultrasonic probe according to the second embodiment of the present invention when seen from a surface horizontal to the axial direction of the pipeline.

FIG. 19 is a diagram illustrating the structure of the ultrasonic probe 14a according to the second embodiment of the present invention when seen from a surface vertical to the axial direction of the pipeline 100. Moreover, FIG. 20 is a diagram illustrating the structure of the ultrasonic probe 14a according to the second embodiment of the present invention when seen from a surface horizontal to the axial direction of the pipeline 100. As illustrated in FIG. 20, since a vibrator surface $S\alpha1$ is inclined with respect to a pipeline contacting surface $S\beta2$, a vibrator projection surface $S\alpha2$ which is a projection surface of the vibrator surface $S\alpha1$ is illustrated in FIG. 19. Since the length L21 in the cross-section, of the vibrator projection surface $S\alpha2$ is smaller than the length L22 in the cross-section, of the pipeline contacting surface $S\beta2$, it is possible to concentrate ultrasonic waves similarly to the first embodiment. An intermediate portion 31a is provided between the inclined surface portion 30a and the pipeline contacting surface $S\beta2$ similarly to the first embodiment.

Modification of Ultrasonic Probe—

In FIGS. 19 and 20, an end surface of the inclined surface portion 30a in the axial direction of the pipeline 100 is vertical to the pipeline 100. However, in an ultrasonic probe 54a which is a modification, illustrated in FIGS. 21 and 22, an end surface of an inclined surface portion 50a in the axial direction of the pipeline 100 is inclined with respect to the pipeline 100.

Figure 21:
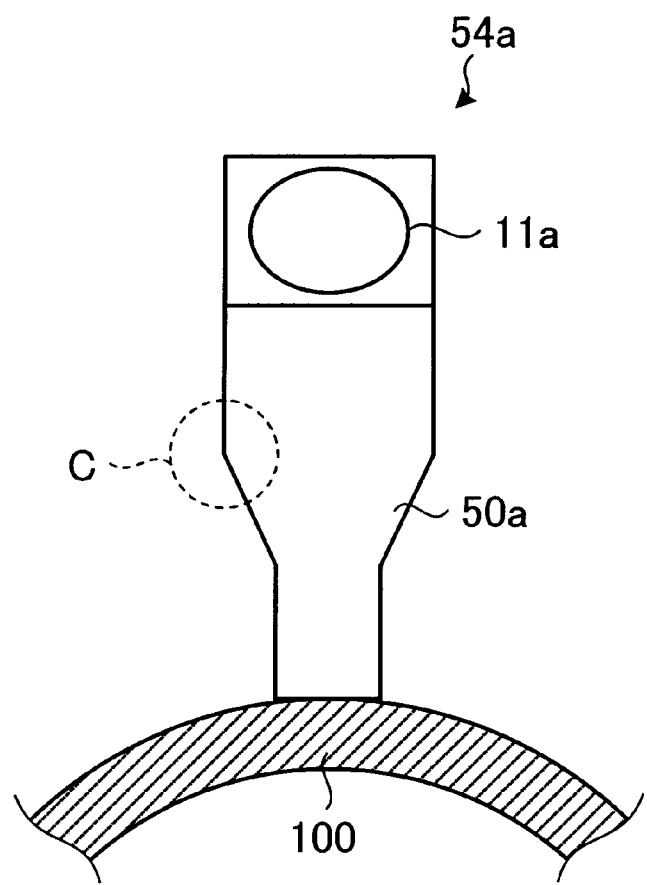
FIG. 21 is a diagram illustrating the structure of an ultrasonic probe according to a modification of the second embodiment of the present invention when seen from a surface vertical to an axial direction of a pipeline.
Figure 22:
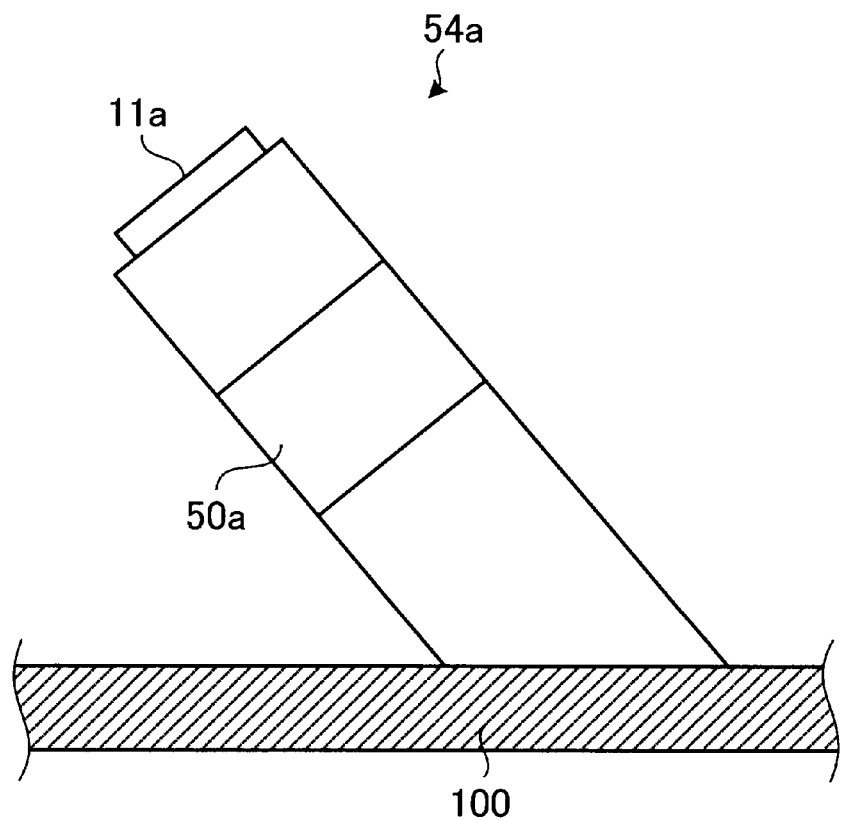
FIG. 22 is a diagram illustrating the structure of the ultrasonic probe according to the modification of the second embodiment of the present invention when seen from a surface horizontal to the axial direction of the pipeline.
Figure 23:
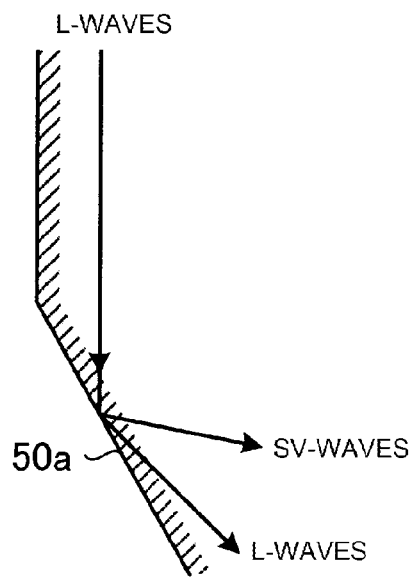
FIG. 23 is an enlarged view of part C in FIG. 21 when L-waves are incident.
Figure 24:
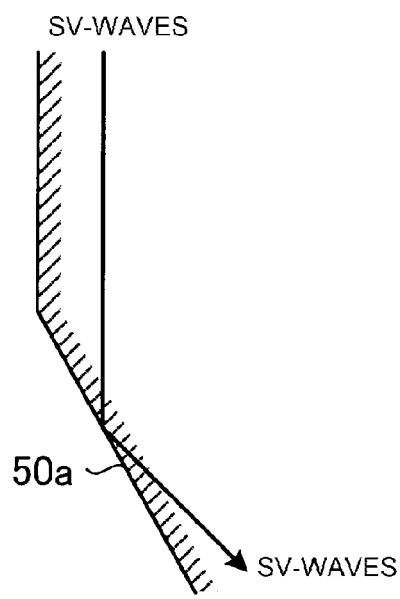
FIG. 24 is an enlarged view of part C in FIG. 21 when SV-waves are incident.
Figure 25:
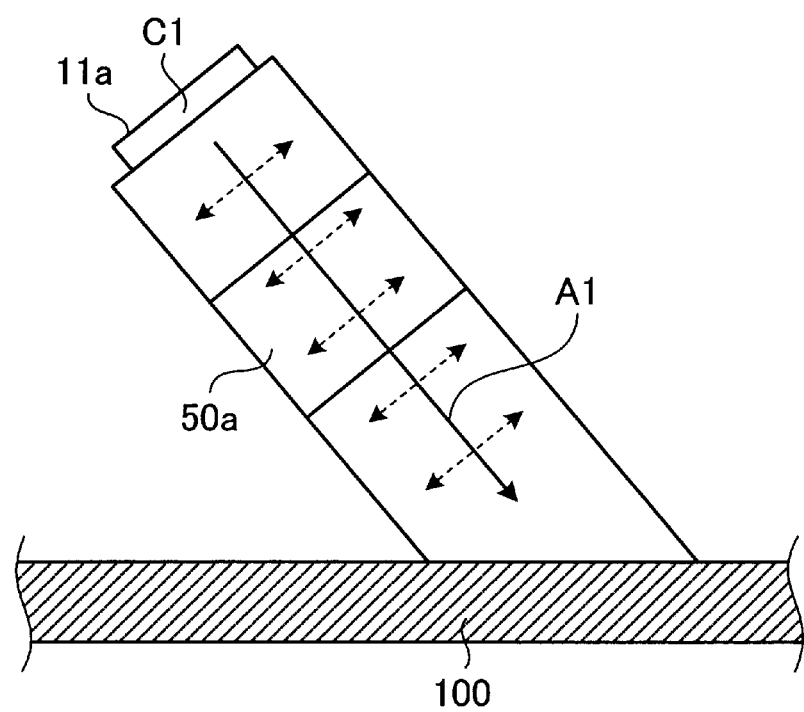
FIG. 25 is a diagram illustrating SV-waves that vibrate in a plane including the center of an ultrasonic vibrator and the axis of a pipeline vertically to a traveling direction of the ultrasonic waves.

Here, FIGS. 23 and 24 are enlarged views of part C in FIG. 21 and illustrate a reflection state of ultrasonic waves on the inclined surface portion 50a. L-waves are longitudinal waves in which a vibrating direction of ultrasonic waves is identical to the traveling direction of ultrasonic waves. Moreover, SV-waves are one of transverse waves which, as illustrated in FIG. 25, vibrate vertically to a traveling direction A1 of ultrasonic waves in a plane including an ultrasonic vibrator center C1 and the axis of the pipeline 100. When the ultrasonic waves generated by the ultrasonic vibrator 11α are L-waves, and as illustrated in FIG. 23, the L-waves are reflected from the inclined surface portion 50a, L-waves and SV-waves are generated in general. Thus, the ultrasonic wave energy is dispersed to the original L-waves and unwanted SV-waves and the original L-waves are attenuated. Due to this, in the present embodiment, the ultrasonic vibrator 11a generates SV-waves as ultrasonic waves. As a result, as illustrated in FIG. 24, the SV-waves are not dispersed on the inclined surface portion 50a, and attenuation of ultrasonic waves can be reduced.

In the second embodiment, the wedge may be formed of a plurality of different materials similarly to the first embodiment. Moreover, the angle θ of the inclined surface portion may be applied by substituting the vibrator surface Sα with the vibrator projection surface Sα2. Further, the arrangement of the ultrasonic absorber 15 may be applied.

EXPLANATION OF REFERENCE NUMERALS 1, 2: Fluid measuring device
10: Measuring unit
11: Ultrasonic vibrator
11a, 11b: Ultrasonic vibrator
12, 12a, 12b, 112: Wedge
13: Ultrasonic connection medium
14, 14a, 14b, 54a: Ultrasonic probe
15: Ultrasonic absorber
20: Main body
21, 41: Transmitting unit
22, 42: Receiving unit
23, 43a, 43b: Switch
24, 44: Time measuring unit
25: Fluid type determining unit
26: Storage unit
27, 47: Input/output unit
28, 48: Control unit
30, 30a, 50a: Inclined surface portion
31, 31a, 32: Intermediate portion
45: Flow velocity measuring unit
100: Pipeline
101: Outer pipeline surface
102: Inner pipeline surface
103: Fluid
130: Flange
A1: Traveling direction
C: Part
C1: Ultrasonic vibrator center
Cp: Velocity of sound
Di: Inner pipeline diameter
Do: Outer pipeline diameter
DT1: Velocity of sound-to-fluid type relation information
DT2: Pipeline material-to-velocity of sound relation information
S: Ultrasonic signal
Sa, Sb, Sc: Reflection wave
Sα, Sα1: Vibrator surface
Sα2: Vibrator projection surface
Sβ, Sβ2: Pipeline contacting surface
ta, tb, tc: Time
td, tf, tu: Propagation time
θ: Angle

What is claimed is:

1. A fluid measuring device which an ultrasonic probe provided on an outer pipeline surface transmits and receives ultrasonic waves to and from fluid in a pipeline to thereby measure characteristics of the fluid based on propagation time of the ultrasonic waves having propagated through the fluid, the fluid measuring device comprising:

a wedge included in the ultrasonic probe and having an ultrasonic vibrator provided on a wedge surface portion inclined and horizontal to a surface contacting the pipeline so that ultrasonic waves enter the fluid vertically, and having a vibrator surface on which the ultrasonic vibrator is provided that has a length in a cross-section vertical to an axial direction of the pipeline, and having a pipeline contacting surface provided in contact with the outer pipeline surface horizontally to the vibrator surface, in the cross-section vertical to the axial direction of the pipeline, that has a length in the cross-section vertical to the axial direction that is smaller than the length of the vibrator surface in the cross-section vertical to the axial direction, wherein the wedge has a shape that is bilaterally symmetrical to a central line that passes through an axis of the pipeline, wherein the inclined wedge surface portion makes an angle θ to a line perpendicular to the pipeline contacting surface, and wherein dividing the length of the pipeline contacting surface in the cross-section vertical to the axial direction by the length of the vibrator surface in the cross-section vertical to the axial direction or a horizontal length of the vibrator surface in the cross-section vertical to the axial direction-provides a value "a" so that a relation of tan 2θ/tan θ<(1+a)/(1−a) is satisfied.

2. The fluid measuring device according to claim 1, wherein at least one of the value "a" satisfies a relation of ⅓<a<1 and the angle θ satisfies a relation of 0°<θ<45°.

3. A fluid measuring device in which a plurality of ultrasonic probes provided on an outer pipeline surface transmits and receives ultrasonic waves to and from fluid in a pipeline to thereby measure characteristics of the fluid based on propagation time of the ultrasonic waves having propagated through the fluid, measured by a time measuring unit that measures time elapsed from transmission to reception of the ultrasonic waves, the fluid measuring device comprising:

a wedge included in the ultrasonic probe and having an ultrasonic vibrator provided on a wedge surface portion inclined with respect to an axial direction of the pipeline so that ultrasonic waves enter the fluid obliquely, and having a vibrator projection surface on which a vibrator surface having the ultrasonic vibrator provided thereon is projected that has a horizontal length in a cross-section vertical to an axial direction of the pipeline, and having a pipeline contacting surface provided in contact with the outer pipeline surface, in the cross-section vertical to the axial direction of the pipeline, that has a length in the cross-section vertical to the axial direction that is smaller than the horizontal length of the vibrator projection surface in the cross-section vertical to the axial direction, wherein the wedge has a shape that is bilaterally symmetrical to a central line that passes through an axis of the pipeline, wherein the inclined wedge surface portion makes an angle θ to a line perpendicular to the pipeline contacting surface, and wherein dividing the length of the pipeline contacting surface in the cross-section vertical to the axial direction by the length of the vibrator surface in the cross-section vertical to the axial direction or a horizontal length of the vibrator projection-surface in the cross-section vertical to the axial direction provides a value "a" so that a relation of tan 2θ/tan θ<(1+a)/(1−a) is satisfied.

4. The fluid measuring device according to claim 3, wherein at least one of the value "a" satisfies a relation of ⅓<a<1 and the angle θ satisfies a relation of 0°<θ<45°.

5. A fluid measuring device in which a plurality of ultrasonic probes provided on an outer pipeline surface transmits and receives ultrasonic waves to and from fluid in a pipeline to thereby measure characteristics of the fluid based on propagation time of the ultrasonic waves having propagated through the fluid, measured by a time measuring unit that measures time elapsed from transmission to reception of the ultrasonic waves, the fluid measuring device comprising:

a wedge included in the ultrasonic probe and having an ultrasonic vibrator provided on a wedge surface portion inclined with respect to an axial direction of the pipeline so that ultrasonic waves enter the fluid obliquely, and having a vibrator projection surface on which a vibrator surface having the ultrasonic vibrator provided thereon is projected, and having a pipeline contacting surface provided in contact with the outer pipeline surface, in a cross-section vertical to the axial direction of the pipeline, wherein the wedge has a shape that is bilaterally symmetrical to a central line that passes through an axis of the pipeline, wherein the inclined wedge surface portion makes an angle θ to a line perpendicular to the pipeline contacting surface, and wherein dividing the length of the pipeline contacting surface in the cross-section vertical to the axial direction by the length of the vibrator surface in the cross-section vertical to the axial direction or a horizontal length of the vibrator surface in the cross-section vertical to the axial direction provides a value "a" so that a relation of tan 2θ/tan θ<(1+a)/(1−a) is satisfied.

* * * * *